United States Patent [19]

Grundy

[11] Patent Number: 4,610,707
[45] Date of Patent: Sep. 9, 1986

[54] BROKEN FILAMENT DETECTOR AND SYSTEM THEREFOR

[75] Inventor: Reed H. Grundy, Murrysville, Pa.

[73] Assignee: PPG Industries, Inc., Pittsburgh, Pa.

[21] Appl. No.: 772,977

[22] Filed: Sep. 5, 1985

[51] Int. Cl.$^4$ ............................................. C08B 21/00
[52] U.S. Cl. ............................................ 65/2; 65/29;
65/158; 73/159; 73/160
[58] Field of Search ................. 65/158, 29, 2; 73/159, 73/160

[56] References Cited

U.S. PATENT DOCUMENTS

| 2,295,795 | 9/1942 | Keeler ................................. 73/160 |
| 2,565,500 | 8/1951 | Ingham, Jr. ................... 73/160 UX |
| 3,303,698 | 2/1967 | Loepfe ................................. 73/160 |
| 4,007,457 | 2/1977 | Aeppli ............................... 73/160 X |
| 4,046,536 | 9/1977 | Smithgall et al. ....................... 65/2 |
| 4,060,965 | 12/1977 | Schwartz ........................... 73/160 X |

Primary Examiner—Arthur Kellogg
Attorney, Agent, or Firm—John E. Curley

[57] ABSTRACT

Detector circuitry and a system for detecting and/or counting transient events such as the passage of broken filament ends in an article such as a fiber glass strand, and for thereby determining the quality of the article being measured, is disclosed. Optical detectors are arranged to produce output pulses for each measured event, and each includes amplifier means and at least one threshold detector for producing a count pulse representing the measured event. Each detector circuit further includes a feedback loop incorporating an integrator and a drive amplifier for the optical detector light source for stabilizing the light output. An alarm is connected to the output of the drive circuit to monitor the light source current level, so as to measure changes in the light output.

Count outputs from the detector circuits are fed to corresponding counters, and at periodic intervals the data contents of the counters are shifted to corresponding latch circuits under the control of a computer or microprocessor. The counters are reset, and the latch circuits are selected sequentially to shift their data contents to corresponding storage locations in the computer or in an external memory such as a disc for processing to obtain an average value for the number of events per unit time or per unit length of an article being measured.

39 Claims, 6 Drawing Figures

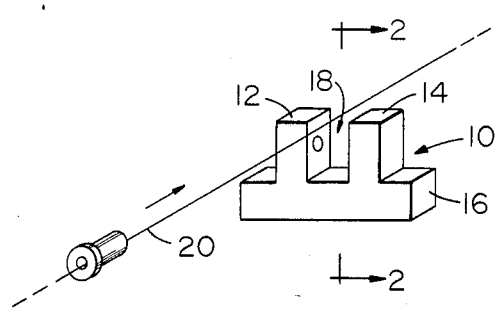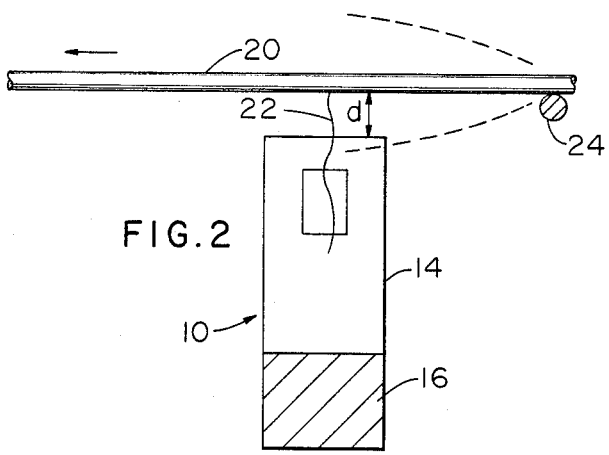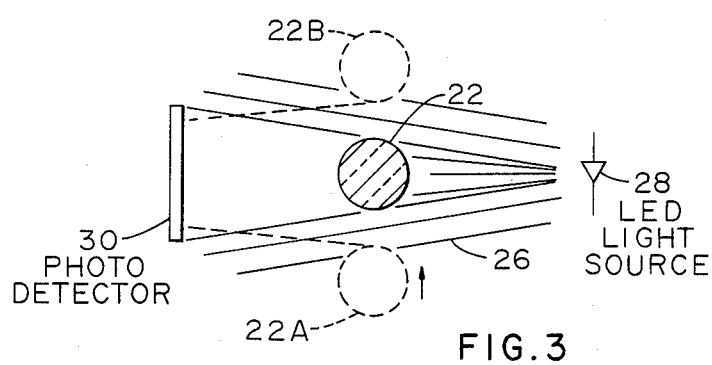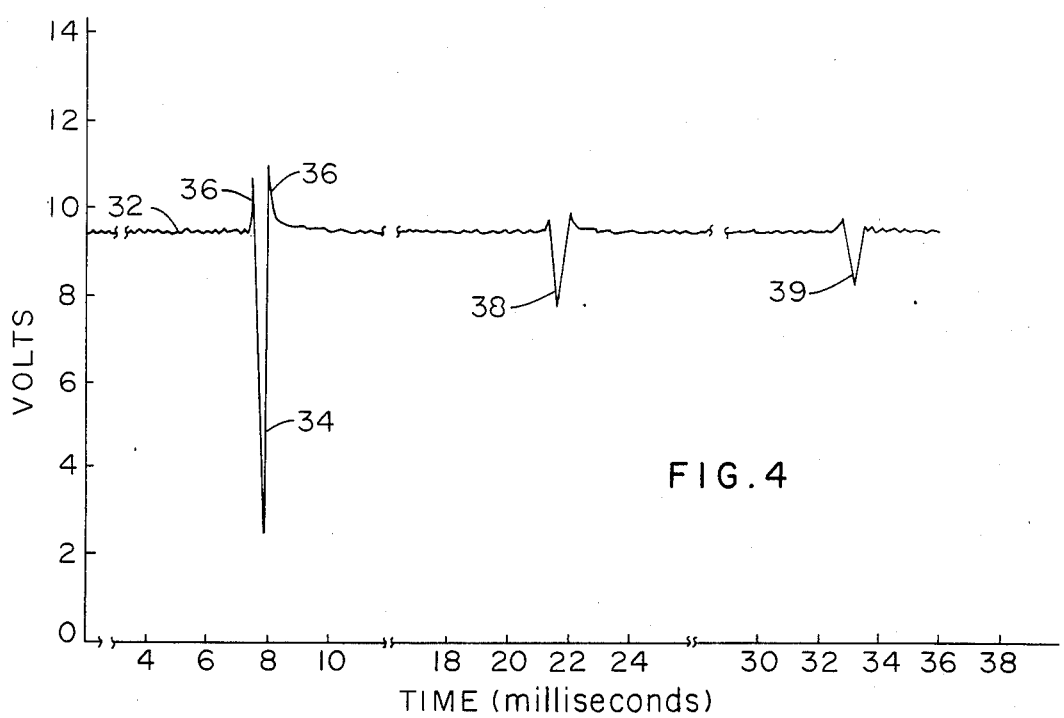

BROKEN FILAMENT DETECTOR AND SYSTEM THEREFOR

BACKGROUND OF THE INVENTION

The present invention relates, in general, to a device for detecting and counting broken filaments in a strand made up of a large number of fiber glass filaments, and, more particularly, to a system for counting such filaments over a long period of time or over a long length of the strand to obtain accurate and statistically significant measurements of the number of broken filaments for use in providing an indication of strand quality and for use in controlling the manufacturing process.

Fiber glass strands typically are formed by drawing a large number of individual filaments from apertures formed in a fiber glass bushing, coating the filaments with a suitable binder, and gathering these filaments into strands which are collected on one or more collets to produce forming packages. The process is carefully monitored to maintain filament diameter and integrity during the high speed drawing process and numerous monitoring systems are known for responding to the breakage of filaments to shut down the process. The strands so formed and collected may be used for many purposes; for example, strands may be drawn from the forming packages and twisted together to form a yarn for use in weaving textiles. The twisted strands are rewound from the forming packages onto bobbins which then supply the yarn to weaving looms or the like. Some of this yarn is rewound onto warp beams for use in the production of fabrics, the yarn on such beams then being used as the warp threads in the fabric being woven. Such yarns must be wound carefully and at precisely controlled tensions on the warp beam in order to ensure a high-quality fabric.

In the processing of the filaments into a strand or processing strands into yarn, the twisting and winding operations produce numerous broken filaments at their surfaces. These broken filaments tend to extend out of the strand or yarn at substantially right angles from the axis of the strand, and not only can adversely affect the quality of the fabric woven therefrom, but can affect the operation of a loom using such yarn, as well. For example, such broken filaments appearing in a cloth used in the production of printed circuit boards can produce small irregularities in the circuit board which can result in short circuits on the printed circuit itself.

Broken filaments can also produce problems in non-fabric applications of fiber glass strand. For example, such strands are often used in the manufacture of insect screens, where the strands are coated with a resin, and the coated strand is passed through an orifice to remove excess resin to limit the diameter of the coated product. Broken filaments on such strands can accumulate in the orifices and eventually block them, thereby degrading the quality of the screening.

The breakage of filaments in a strand may be the result of the twisting, rewinding, and other mechanical handling of the strand, and thus the quantity of broken filaments can provide a guide as to whether the handling equipment is operating properly. More importantly, however, the breakage of filaments provides an indication of the quality of the fiber manufacturing process, and, accordingly, the amount of breakage that occurs can be used in the control of the various parameters of a fiber-making process. There are about 30 to 40 variables in this process, including the temperature of the bushings at the orifices, the temperature of the glass, the materials in the melt, and the like. Variations in these parameters can cause very subtle changes in the filaments which can show up as a change in the amount of breakage that is occurring in the strands.

Thus, it is desirable to get an accurate measure of filament breakage in strands, in order to monitor both the manufacturing process and the mechanical handling of the glass so as to enable both the manufacturer of the filaments and the manufacturer of the products made therefrom to provide quality assurances to their respective customers.

The breakage of filaments in a strand has been found to be of an extremely random nature, however, with the number of filament breaks per unit length of strand varying widely not only on a single bobbin, but also between a number of bobbins drawn from the same forming package, or between packages drawn from the same fiber glass melt. The random nature of this breakage makes it very difficult to know with any confidence whether a particular measurement, taken from a relatively short strand length, is anywhere close to the average amount of breakage for the strand on a bobbin, for example, for it is very difficult to even determine what that average amount might be. Accordingly, it has not been possible in the past to determine from measurements of filament breakage whether a change in the manufacturing process or in the handling of the fiber has had any significant effect on breakage, or whether a given measurement is simply within the normal variation to be expected with random distribution. It has been possible to obtain a value for filament breakages over selected lengths of strands with existing measuring devices, but such measurements have been of little value since they were extremely slow, and, therefore, provided statistically insignificant readings which could not realistically be compared to a significant average value, since the latter value was not available. Therefore, although it was known that filament breakage was a problem, and although various devices have been provided in the past to measure the quality of fiber glass strands and yarns, the prior art has not provided a device or system for providing statistically accurate mean or average values of filament breakage, which would permit accurate measurements of this aspect of the quality of the fiber glass strands being provided to a customer.

U.S. Pat. Nos. 3,729,635 and 4,184,769 are examples of prior art devices and systems for detecting defects in yarn through the use of optical sensors. In both patents, the yarn is passed through a sensor, with the output of the sensor varying in accordance with the thickness of the yarn. In accordance with U.S. Pat. No. 3,729,635, if more than a predetermined number of variations, or faults, occurs within a unit time, the winder, which may be a warp beam, stops to allow visual inspection of the yarn. In a similar manner, the device of U.S. Pat. No. 4,184,769 generates a defect signal upon detection of a predetermined number of faults. Devices of this type provide continuous measurements of the variation of thickness of a yarn or strand, and, in order to minimize errors, the light transmitters for such devices must be driven by carefully regulated power supplies, with expensive beam splitters to provide feedback control being utilized in some such units. Furthermore, expensive optics and complex circuitry are required to obtain the degree of accuracy required to insure that the analog output signals are proportional to the thickness of the yarn, and that the system will respond even to very slowly changing conditions which produce essentially a DC output. Such measuring devices, besides being expensive, typically are quite slow, being capable of measuring only about 80 meters of strand per minute. Because of this slowness, it is usual to take samples only at selected points within a bobbin as it is being unwound, with measurement typically being made at three or four points within the bobbin. Because of the random nature of filament breakage, such measurements do not provide an accurate picture of the quality of the strand, but, rather, produce results which are not much improved over a simple visual inspection of the outside layer of a bobbin.

SUMMARY OF THE INVENTION

It is, therefore, an object of the invention to provide a method of determining broken filaments in fiber glass strands and accurately identifying the location of the broken filaments and their frequency in a given length of strand.

It is a further object of the invention to process faults detected in a moving strand or article having random faults to locate the faults, record the number of faults and their location and/or to average the faults per unit of length.

It is another object of the present invention to provide an improved optical apparatus and circuitry for providing accurate, reliable, high-speed measurements of transient effects such as filament breakage in fiber glass strands.

It is another object of the invention to provide an optical detector and circuitry for detecting broken filaments in a fiber glass strand, and for providing a count of such broken filaments over a long period of time in order to obtain accurate, statistically significant measures of filament faults.

It is another object of the present invention to provide a multiplexed system of optical measurements for obtaining a statistically accurate and reliable determination of the quantity of broken filaments in a fiber glass strand.

It is another object of the present invention to provide an accurate determination of the relative quality of the fiber glass strands in a package to provide accurate manufacturing process control, and to permit reliable quality determinations.

It is a still further object of the present invention to provide an optical system for measuring filament breaks in a strand without the need for measuring the strand itself, but only the broken filament ends, thereby permitting digital processing of the output from the optical system.

In accordance with a preferred form of the present invention, there is provided at least one optical detector which is located adjacent the path of a strand to be measured. The strand is guided past the detector so that the strand itself does not pass through the optical path of the detector, but sufficiently close that any broken filaments which extend out from the surface of the strand will pass through it. Preferably, the optical detector includes a light emitter and a light detector, with the broken filaments passing through the light path defined therebetween to produce output pulses from the detector. Such pulses will have amplitudes which are proportional to the diameters of the filaments, assuming that the filaments extend across the entire width of the beam.

The output of the light detector is fed through an amplifier and to a feedback circuit to regulate the current flow to the light source, thereby to regulate the intensity of the beam and maintain it at a preset level in the absence of a broken filament end. The output of the amplifier is also supplied to a threshold detector, the output of which is supplied to a counter. When a filament passes through the light path, it interrupts the light beam and the output of the photodetector changes, producing an output pulse which is of an amplitude proportional to the thickness of the filament and of a width proportional to the speed with which the filament passes through the light beam. If this output pulse is of sufficient amplitude, the threshold detector supplies an event pulse to the counter. Suitable buffer means may be provided between the output of the threshold detector and the counter for pulse shaping, in order to ensure the accuracy of the count.

Periodically, the content of the counter is shifted to a latch circuit, the counter is reset and starts to count again, and the content of the latch is supplied to a suitable storage location for future processing.

In an application such as the winding of multiple lengths of yarn onto a warp beam, a large number of detectors and counters are provided, one for each length of yarn, and multiplexing circuitry is provided to transfer the data in each of the corresponding latch circuits sequentially to corresponding storage locations; for example, in a microprocessor or computer.

Because the detector is measuring only transient pulses, the device of the present invention is capable of very high speed operation, measuring a strand at the rate of 500 yards or more per minute. Furthermore, the entire length of a strand can be measured, with periodic readings of the number of broken filaments being obtained. For example, readings can be obtained for every 1000 yards of strand, the counting and latching circuitry storing this data for subsequent averaging of the output over lengths of as much as 80,000 yards for a single bobbin. The more measurements that are made, the more accurate and reliable is the calculation of an average or mean value for the number of filament breaks per unit length of strand, so that a statistically sound basis for comparison of the strands obtained, for example, from different forming packages, can be obtained by measuring the number of breaks in the bobbins rewound from each package.

Although in the preferred form of the invention, only a single threshold detector is utilized at the output of a given light detector, it may be desirable, in some instances, to provide a series of threshold devices, each set at a different level, so as to provide a plurality of outputs, each proportional to the number of filaments of a predetermined size. Thus, for example, if eight threshold detectors are provided, filaments of eight different size ranges can be detected to permit further analysis of the filaments.

The device of the present invention is relatively inexpensive, yet it provides filament measurements a high degree of statistical accuracy and reliability, thereby allowing usage of the system to monitor the quality of the strand being produced, as well as to detect the effects of changes in the manufacturing process. Thus, for example, if a first strand is manufactured under a first set of conditions, the present invention will provide a statistically accurate average value of the number of breaks per unit length of the filaments contained in that strand. Thereafter, a second strand, made after a change in one of the manufacturing parameters, can also be measured, and a statistically accurate average value of the filament breakage obtained for that second strand. Because the two measurements are reliable, it is possible to determine with great reliability the effect of the change in the process parameters so that much more effective control of the manufacturing process can be obtained.

BRIEF DESCRIPTION OF THE DRAWINGS

The foregoing and additional objects, features, and advantages of the present invention will become apparent to those of skill in the art from a consideration of the following detailed description of preferred embodiments thereof, taken in conjunction with the accompanying drawings, in which:

FIG. 1 is a perspective view of an optoelectronic module arranged for detection of broken filament ends;

FIG. 2 is an enlarged cross-sectional view of the module taken along lines 2—2 of FIG. 1;

FIG. 3 is a diagrammatic illustration of a light interruption pattern in the module of FIG. 1;

FIG. 4 is a diagrammatic illustration of an oscilloscope trace showing the output from the module of FIG. 1 for various diameters of broken filaments;

DETAILED DESCRIPTION OF THE PREFERRED EMBODIMENTS

Figure 5:
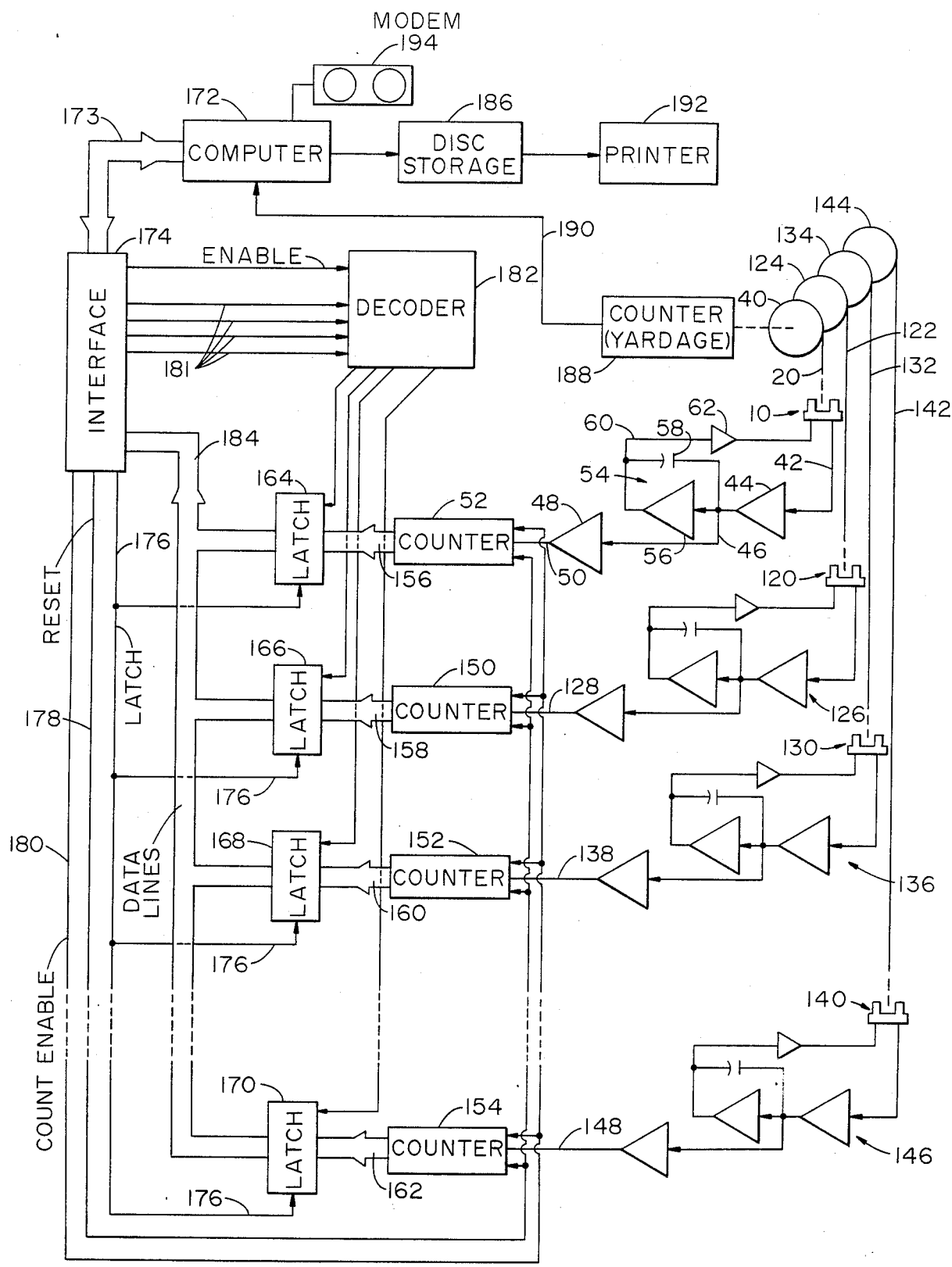
FIG. 5 is a block diagram of the circuitry for the system of the present invention.

Turning now to a more detailed consideration of the present invention, there is illustrated in FIG. 1 an optoelectronic module 10, which is a commercially available optical detector. The module 10 includes a pair of upstanding legs 12 and 14 supported on a base 16, and spaced apart to define a measuring channel 18. A suitable light source such as a light-emitting diode (LED) (not shown) is mounted in one of the upstanding legs; for example, leg 12, while a suitable light detector, such as a phototransistor (not shown), is mounted in the other leg; for example, leg 14. The LED and the light detector define a light path across channel 18, and circuit means (to be described) is provided to respond to the output of the light detector and to produce an output pulse whenever the light beam is interrupted. A strand or length of yarn 20, which is to be monitored for the presence of broken fibers, is so located as to pass over the detector channel 18 of the module 10. As illustrated in FIG. 2, the path of the strand is preferably flush with the top of the module 10, but centered over the channel 18, so that the strand itself does not interrupt the light beam, but so that any broken filaments extending from the strand, such as the filament 22 illustrated in FIG. 2, will pass through the beam for detection. As previously explained, strand 20 is made up of a large number of filaments twisted together to form a unitary strand having the desired thickness and strength characteristics. In the manufacture of such strand, which may involve twisting together of numerous filaments, or during the winding and rewinding operations which occur in the transfer of the strand to a bobbin and then to a warp bar, for example, some of the filaments may break. Such breakage may be due to excessive mechanical stresses during the winding or twisting operations, or may be due to faulty filament structure caused by a problem in the manufacturing process. In either case, the existence of such broken filaments degrades the quality of the strand, so it is extremely desirable to detect them, and to determine the effect that they have on the overall quality of the material, by determining the number of broken filaments per unit length of the strand to a high degree of accuracy and reliability. Since the number of broken filaments per unit length may be an indication of the quality of the filaments themselves may reflect change or errors in manufacturing parameters, so the accurate detection of such filaments is an important factor in process control.

Since broken filament ends tend to extend out of the strand at approximately right angles to the axis of the strand when they break, it has been found that the strand does not have to pass through the detector channel 18, but, instead, can be located outside the detector module, as shown in FIG. 2. In tests, it has been found that the distance between the top of the detector 10 and the strand 20 should be between zero and one millimeter. The strand preferably is supported by a smooth guide rod 24 located upstream from the detector to prevent transverse motion of the strand due to vibrations and the like from carrying the strand itself into the path of the light beam. Because the guide rod tends to collect pieces of broken filament which could reach into the channel 18 and affect the output of the light detector, it is preferred that the guide rod be at least 5 cm away from the detector module.

It will be understood that the broken filament ends 22 may extend in any direction radically outwardly from the strand 20, so that not all of the broken filaments will pass through the light beam for detection. However, the detector will sense a large proportion of the filaments, and since over a long length of strand the broken ends will tend to be uniformly distributed around the circumference of the strand, although randomly distributed along its length, the reading obtained by the module 10 will be directly proportional to the total number of broken filament ends. Accordingly, an accurate count for purposes of determining the quality of the strand, and for determining the effect on breakage of changes in the manufacturing process or in the handling of the strand, will be provided by the present invention.

The module 10 is a very high-speed device, and is capable of measuring filaments which pass through the light path at a high rate. As shown in FIG. 3, the filament end 22 interrupts the light beam 26 in the path between the light source 28 and a detector 30. The passage of the filament 22 through the light beam produces at the detector output a pulse 32, illustrated in FIG. 4, the width of the pulse being dependent on the speed of the filament and its amplitude being dependent on the diameter of the filament.

FIG. 4 is a diagrammatic illustration of an oscilloscope trace of the output from detector 30. The detector normally produces an output 32 at a level determined by the intensity of source 28, with the pulse 34 being produced by a filament 0.0016 inch in diameter passing through the light beam 26. It will be noted that small positive peaks 36 occur before and after the negative going pulse 32, which peaks are caused by light reflection from the surface of the filament at positions 22A and 22B as the filament approaches the light beam 26 and as it leaves it.

FIG. 4 also illustrates at 38 and 39 the pulses produced by smaller diameter filaments, pulse 38 being produced by a filament 0.0003325 inch in diameter, the pulse 39 being produced by a filament 01000275 inch in diameter. It will be understood that reduced amplitude pulses could also be produced by filament ends that do not extend all the way through the light beam in the vertical direction.

The circuit and system for responding to the pulses produced by filaments passing through the light beam 26 is illustrated in FIG. 5, to which reference is now made. The optoelectronic module 10 is associated with amplifier strand 20 which may be supplied from a suitable bobbin 40. The strand passes by the module in the manner described above, and the photosensitive detector 30 carried by the module produces an output signal on line 42. This signal is fed through an operational amplifier 44, the output of which is a series of pulses, such as the pulse 32 illustrated in FIG. 4. These pulses, which indicate the presence of broken filaments, are supplied by way of line 46 to a threshold detector 48 which is set to a predetermined level so that only pulses which exceed that level will produce an event pulse on detector output line 50. Thus, the threshold detector 48 serves to eliminate noise and the like which might provide a false reading of the number of broken filaments. The event pulse on output line 50 is supplied to a suitable counter 52 which then counts the number of filament ends detected by module 10.

It has been found that over a period of time the intensity of the light beam 26 may decline; accordingly, a feedback loop is provided to compensate for that decline. One of the reasons for the decline is the fact that the strand 20 normally is coated with a protective binder material. During the processing of the strand, some of the binder material may be scraped off, as by the support 24, and such material can collect on the optics of the module 10, reducing the intensity of the light beam. The feedback loop to compensate for this consists of an integrator circuit generally indicated at 54 and including an amplifier 56 and a parallel capacitor 58. The output of the integrator circuit is supplied by way of line 60 to a driver amplifier 62 which in turn supplied power to light source in the detector. As the intensity of the light beam declines, the output of the drive 62 is increased by the integrator circuit 54 to produce a higher output from the light source, thereby restoring the light beam to its preset intensity. A low pass filter circuit could be used in the feedback loop in lieu of the integrator circuit but is not preferred.

Figure 6:
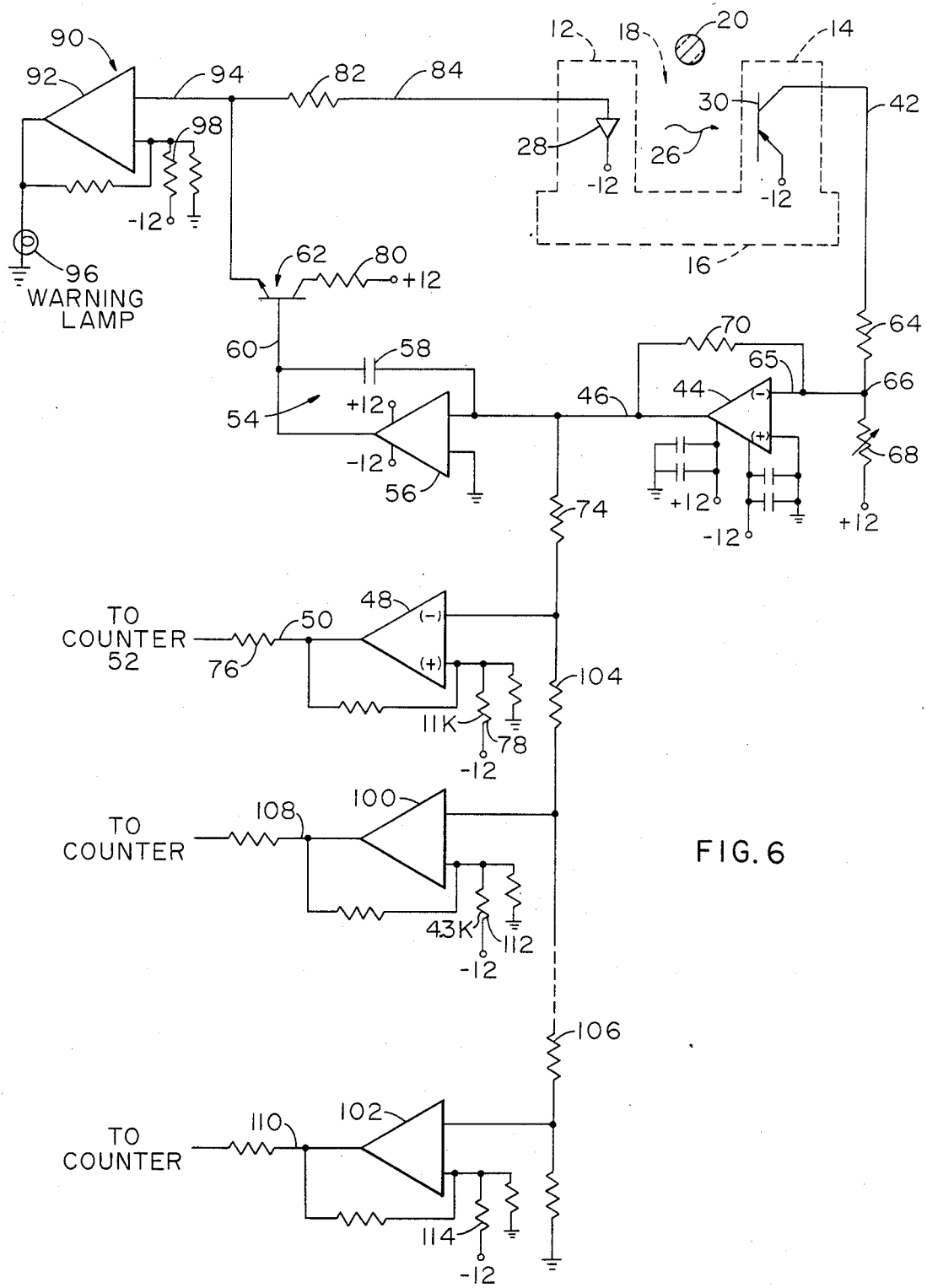
FIG. 6 is a schematic diagram in partial block form of the filament detector circuitry.

The filament detector circuitry shown in block diagram form in FIG. 5 is illustrated in more detail in FIG. 6, where the light source 28 is shown as an LED mounted within the leg 12 of module 10 to produce a light beam 26 across the detector channel 18. The light beam strikes a light detector such as a phototransistor 30, which includes a grounded emitter and a collector connected to the output line 42. Line 42 includes a voltage divider resistor 64 and is connected, in this illustration, to the negative input 65 of operational amplifier 44. Also connected to this input, by way of junction 66, is a variable bias resistor 68 by means of which the normal output of the amplifier 44 is established in the absence of a filament end. This normal output level is illustrated in FIG. 4 at 32, as explained above. A feedback resistor 70 is connected from the output 46 of amplifier 44 to the input 65.

Output line 46 is connected through limiting resistor 74 to the negative input of a threshold detector 48, the output of which is connected by way of line 50 and resistor 76 to the counter 52. The positive input of threshold detector 48 is connected through bias resistor 78 to a source of negative bias voltage, the size of the resistor 78 determining the threshold at which the detector becomes conductive to produce an output pulse on line 50.

The signal on line 46 from the operational amplifier 44 is also supplied to the integrator network 54, which includes the operational amplifier 56 and the capacitor 58. The output of the integrating circuit is applied by way of line 60 to the base of a driver transistor 62, the collector of which is connected through resistor 80 to a source of bias voltage and the emitter of which is connected through a resistor 82 and line 84 to the LED 28 to supply the drive current for the LED device. A portion of the current output from detector 30 thus is fed back through operational amplifier 44 and the integrator circuit 54 to regulate the conductivity of drive transistor 62, the integrating network 54 serving to smooth out the effects of the pulses 32 produced by the passage of broken filaments through the light beam and to stabilize the drive current to the LED. As the normal current 32 (FIG. 4) from the detector gradually decreases degrees, for example, because of aging of the LED or because of an accumulation of dust, binder material, or the like on the optics of the module 10, the bias applied to amplifier 44 through variable resistor 68 will change the amplifier output appearing on line 46. This change then varies the output produced by the integrator network 54 to increase the current flow through driver transistor 62, thus restoring the output of the LED to its preset intensity level. In this way, the integrator circuit 54 and the driver transistor 62 keep the intensity of beam 26 constant in the absence of a filament. If desired, a level detector 90, including an operational amplifier 91 connected by way of line 94 to the input to the LED at line 84, may be provided to sense the current being supplied to the LED. The output of amplifier 92 may be connected to a warning lamp 96 to provide an indication when the current level to the LED exceeds a predetermined value, set by the bias resistor 98 connected to a second input to amplifier 92.

The circuit of FIG. 6 as thus far described provides an output signal on line 50 each time an event pulse 34 occurs which exceeds a predetermined amplitude, and provides a count of filament ends where the filaments exceed a preselected diameter. If desired, a plurality of similar threshold circuits may be provided, as indicated by the threshold circuits 100 and 102. These circuits receive their inputs from line 46 through respective limiting resistors 104 and 106, and produce outputs on their corresponding output lines 108 and 110. The pulse amplitude to which each threshold detector responds is determined by the bias resistors 112 and 114, respectively. By proper adjustment of the bias resistors 78, 112, and 114 for the threshold detectors 48, 100, and 102, these circuits can produce output pulses to respective counters to produce event pulses corresponding to selected filament sizes so that a measure of the distribution of filament diameters measured by a single detector 10 can be obtained.

FIG. 6 illustrates the circuitry for a single optoelectronic module 10 which measures the presence of broken filaments in a single strand 20. Module 10 and its circuitry constitute a single detector unit. As illustrated in FIG. 5, a plurality of such units may be provided, each measuring a different strand being supplied from a different bobbin. Thus, for example, the module 10 provides a measure of strand 20, a second optoelectronic module 120 with its associated circuitry may be arranged to measure a second strand 122 supplied from a bobbin 124, a third optoelectronic module 130 may be provided to measure a third strand 132 supplied by a third bobbin 134, and so on, with a module 140, representing an nth optoelectronic module, measuring a corresponding strand 142 supplied by a bobbin 144. Each of the modules 120, 130 and 140 is connected to a corresponding detector circuit generally indicated at 126, 136, and 146, respectively, each of which is similar to that illustrated in FIG. 6, and each of which produces a train of output event pulses on its corresponding output line 128, 138, and 148, respectively. The train of event pulses on each of these output lines represents the number of broken filaments on the corresponding strands 122, 132 and 142.

As previously stated, the train of output pulses on line 50 is supplied to a corresponding counter 52. In similar manner, the outputs on lines 128, 138, and 148 are connected to corresponding counters 150, 152 and 154, respectively, to provide continuous counts of the random event pulses being provided by their respective detector units.

Although the output lines 50, 128, 138, and 148 are shown as being directly connected to their corresponding counters 52, 150, 152, and 154, it may be desirable, in some instances, to incorporate suitable buffer amplifiers (not shown) in those lines to shape the pulses before they are supplied to the respective counters.

The data in each of the counters is supplied by way of data line 156, 158, 160, and 162, respectively, to corresponding latch circuits 164, 166, 168, and 170. Under the control of a suitable computer 172, which may be a Hewlett-Packard Model HP218, for example, and through data line 173 and an interface network 174, the latching circuits are periodically activated to latch the event count data then in the respective counters. The latching signal is provided by way of line 176 to each of the latch networks. The latching signal is followed by a reset signal on line 178 which is applied to each of the counters 52, 150, 152, and 154, to reset them to zero after the counter content has been latched. Thereafter, a count enable signal is provided by the control computer on line 180 to restart each of the counters.

After the data in the counters has been latched, the computer 172, by way of interface 174 and data lines 181, activates a decoder 182 which operates to sequentially select each of the latches, in turn, to transfer the data contained therein by way of data lines 184 through the interface 174 and data lines 173 to computer 172. The data so obtained from the counters is stored at the computer, for example, in a suitable disk storage 186 together with data concerning the length of the strand supplied to the individual detector units. Strand length data may be obtained by way of strand length counter 188, by bobbin weight, or by any other conventional manner. This data is supplied to the computer 172 by way of line 190 and enables the computer to determine, among other things, the latching period of the data, and, ultimately, the number of broken filaments counted per unit length of the strand being monitored or the number of yards between each broken filament detected. For example, counter 52 can be a 1 bit (flip flop) binary counter and the computer cycle time can be made sufficiently small so as to eliminate the possibility of two broken filaments occuring within one cycle. Upon detection of a broken filament by a given counter, the accumulated yards in the yardage counter 188 is recorded and stored for the data associated with that counter. Subsequent events are similarly recorded by counter 188. If desired, the information obtained by the computer may be printed by a printer 192 or may be supplied by way of a modem 194 to a remote location for storage and further processing. The yardage counter 188 may be any conventional counter and may be sensitive either to the motion of the strand or the rotation of the drive capsten 34 on which the strand is moved. Individual counters may be provided for each strand, or one counter may be used to provide a single reading which may then be used for the calculations for all of the strands.

By utilizing a high-speed detector and high-speed digital circuitry, the system of the present invention is capable of obtaining an accurate count of the number of broken filaments over a relatively long period of time, so that highly accurate measurements of the average number of breaks in a unit length of strand can be obtained. It has been found that, because of the random nature of filament breakage, in order to accurately and reliably detect a 10 percent difference in quality between strands, it is necessary to obtain a count of the number of broken filaments in 0.85 million yards of fiber glass strand. If it is desired to increase the resolution of the system so as to be able to detect a 5 percent difference in quality with a high degree of reliability, it is necessary to obtain measurements from 3.4 million yards of strand. In order to increase the resolution to detect a 1 percent different in quality between two strands, it is necessary to measure 104.3 million yards of strand. Such measurements would not be practical with prior art systems, since they are far too slow to permit the measurement of the quantity of strand indicated. However, with the present invention, even very subtle changes in the manufacturing process of the fibers, such as would produce only a 1 percent change in the amount of filament breakage, can readily and accurately be detected, thereby allowing far superior control of the manufacture and processing of fiber glass strands.

Although the present invention has been described in terms of a broken strand detector, it will be apparent that it is equally useful in determining the quality of yarn formed from multiple strands. Furthermore, as explained with respect to FIG. 6, the system is also able to obtain for each strand being measured a distribution of the diameters of the broken filaments by providing additional threshold detectors with corresponding counters. The output of those additional counters would also be connected to corresponding latching networks, and connected to the computer for selection and storage in the manner described with respect to FIG. 5.

A further use of the present system is in the detection of and measurement of the amount of binder material which is shed by the strand as it passes by the detector. The threshold detector 90 which measures the change in the level of the drive current to the LED 28 and provides a warning signal when that current exceeds a predetermined value also provides a measure of the time period over which a predetermined change in intensity occurs, thereby providing a measure of the amount of binder being shed by the strand during that time.

It should also be noted that the detector units of the present invention may also be used to measure strand dimensions by moving the strand periodically into the detector channel and through the light beam 26. This motion of the strand itself will produce an output pulse, the amplitude of which can be used to determine the diameter of the strand. Furthermore, if desired, a pair of such detectors may be provided at right angles to each other for measuring the diameter of the strand in two directions, so as to determine strand flatness, or aspect ratio.

In order to obtain an accurate measure, the data in the counters 52, 150, 152, and 154 is latched at fixed increments. These increments can be determined by time; for example, once each minute, or may be determined by a predetermined length of the strand being measured; for example, every 500 yards. A preferred increment is the yardage count obtained from counter 188 so that accurate measurements are obtained even if the strands should stop in the middle of a count. In such a situation, the computer would simply wait until the strands restarted, and the proper yardage count was obtained, before latching the contents of the pulse counters 52, 150, 152, and 154, thereby ensuring accurate data.

In describing the method of the instant invention, the preferred optoelectronic detector system has been described. It will be understood, however, that the method may be practiced using other detector means such as sonic devices, since the method involves the accumulation of yardage counts as well as detected faults, the accumulation of that data, and other such steps in the method as recited by the accompanying claims involving processing the collected data.

Although the present invention has been described in terms of strands being rewound from a bobbin onto a warp beam, it will be apparent that the system can be used in other locations in the processing of fiber glass strands or yarns. For example, it may be desirable to use two detector units on a single strand, one being located before and the other after a processing step, such as before and after winding on a bobbin, in order to detect the breakage which is produced by that particular process, and to determine the effectiveness of the binder used on the strand.

Finally, while the present invention has been described in terms of preferred embodiments, it will be apparent that numerous variations and modifications may be made without departing from the true spirit and scope thereof, as set forth in the following claims.

I claim:

1. A method of determining with a high degree of reliability and accuracy the quality of an elongated article having random faults such as filament ends projecting outwardly therefrom, comprising:
    moving an article to be measured at a high rate of speed along a path;
    positioning a detector including a beam detecting source adjacent said path, said detector and its beam being sufficiently far from said path as to prevent the article from activating said beam detecting source but sufficiently close to enable random faults to pass through and activate said beam detecting source to produce corresponding event pulses;
    accumulating a yardage count for each of said event pulses recorded by an event pulse counter;
    transferring the yardage counts to a first storage location and resetting said event pulse counter; and
    transferring each stored yardage count from said first storage to a second, processing, storage location.

2. The method of claim 1, wherein the detector is an optoelectronic detector and the detecting source is a light beam and a light detector which are positioned so that the article does not interrupt the light beam and activate the said detecting source but random faults in the article do interrupt the light beam to thereby activate the light detector to produce a corresponding event pulse.

3. The method of claim 1, wherein the yardage counts stored in the processing storage location are processed therein to obtain the yardage location of each detected event pulse.

4. The method of claim 1, wherein the yardage counts stored in the processing storage location are processed therein to obtain an average of detected event pulses per unit length of said article.

5. The method of claim 2, wherein the yardage counts stored in the processing storage location are processed to obtain the yardage location of each detected event pulse.

6. The method of claim 2, wherein the yardage counts stored in the processing storage location are processed therein to obtain an average of detected event pulses per unit length of said article.

7. The method of claim 1, wherein said counts of said event pulses are accumulated and transferred over a sufficient length of said article to permit determination of a statistically significant average value of events per unit of length, whereby an accurate and reliable measure of quality can be obtained from a randomly occurring event.

8. The method of claim 7, wherein said counts of said event pulses are accumulated and transferred over a length of said article on the order of one million yards, whereby quality differences of about 10 percent can be determined.

9. The method of claim 7, wherein said counts of said event pulses are accumulated and transferred over a length of said article on the order of 100 million yards, whereby quality differences of about one percent can be determined.

10. The method of claim 7, wherein said event pulses vary in amplitude in accordance with a selected characteristic of detected faults, and wherein the step of accumulating a count of said event pulses includes separating said event pulses by pulse amplitude and thereafter accumulating said separated event pulses in a plurality of corresponding level counters, whereby the counts in the said level counters represent the variations in said selected characteristics.

11. The method of claim 2, wherein said counts of said event pulses are accumulated and transferred over a sufficient length of said article to permit determination of a statistically significant average value of events per unit of length, whereby an accurate and reliable measure of quality can be obtained from a randomly occurring event.

12. The method of claim 11, wherein said counts of said event pulses are accumulated and transferred over a length of said article on the order of one million yards, whereby quality differences of about 10 percent can be determined.

13. The method of claim 11, wherein said counts of said event pulses are accumulated and transferred over a length of said article on the order of 100 million yards, whereby quality differences of about one percent can be determined.

14. The method of claim 11, wherein said event pulses vary in amplitude in accordance with a selected characteristic of detected faults, and wherein the step of accumulating a count of said event pulses includes separating said event pulses by pulse amplitude and thereafter accumulating said separated event pulses in a plurality of corresponding level counters, whereby the counts in the said level counter represent the variations in said selected characteristics.

15. The method of claim 2, further including sensing the intensity of said light beam and regulating said light beam to maintain the sensed intensity at a predetermined level.

16. The method of claim 2 further including sensing the intensity of said light beam and regulating said light beam by electrically integrating the difference between the desired light detector activation output and the actual light detector activation output in a feedback circuit which electrically reduces the integrated difference to zero.

17. The method of claim 16, further including monitoring the current supplied to said optoelectronic detector to obtain a measure of the rate at which the intensity of said light beam changes.

18. The method of claim 1 further including:
moving a plurality of articles simultaneously along spaced paths;
locating a corresponding detector adjacent the path of each of the said articles to produce corresponding event pulse outputs;
separately accumulating a yardage count for each of said event pulses recorded by separate event pulse counters associated with each said article;
transferring each of the yardage counts to a corresponding first storage location and resetting the event pulse counter associated with that yardage count;
and separately transferring said counts from said corresponding first storage locations to a processing storage location.

19. The method of claim 2 further including:
moving a plurality of articles simultaneously along spaced paths;
locating a corresponding optoelectronic detector adjacent the path of each of the said articles to produce corresponding event pulse outputs;
separately accumulating a yardage count for each of said event pulses recorded by a separate event pulse counter associated with each said article;
transferring each of the yardage counts to a corresponding first storage location and resetting the event pulse counter associated with that yardage count;
and separately transferring said counts from said corresponding first storage location to a processing storage location.

20. The method of claim 18, wherein the yardage counts for each article storage in the processing storage location are processed therein to obtain the yardage location of each detected event pulse for each article.

21. The method of claim 18, wherein the yardage counts for each article stored in the processing storage location are processed to obtain an average for each detected event pulse per unit length of each of said articles.

22. The method of claim 19, wherein the yardage counts for each article stored in the processing storage are processed therein to obtain the yardage location of each detected event pulse for each of said articles.

23. The method of claim 19, wherein the yardage counts for each article stored in the processing storage location are processed to obtain an average for each detected event pulse per unit length of each of said articles.

24. Detector apparatus for determining with a high degree of reliability and accuracy the quality of an elongated article having random faults such as filament ends projecting therefrom, comprising:
an optoelectronic detector having a light source and a light receiver defining a light beam;
means for guiding an article to be measured along an article path past said detector and its light beam, said detector light beam being spaced from said article path sufficiently to prevent the article from interrupting said light beam, but being sufficiently close to said article path to enable random faults such as filaments ends projecting from the article to interrupt said light beam;
circuit means connected to said light receiver to produce an event pulse for each interruption of said light beam, said circuit means including amplifier means connected to said light receiver, and level detector means having a predetermined threshold and being connected to the input of a storage means which level detector means produces an event pulse whenever its threshold is exceeded;
an integrator connected to the amplifier means to provide an integrator output which automatically regulates the light in said light source to maintain a predetermined amount of electrical output from the light receiver.

25. The method of claim 1, wherein said article is a fiber glass strand, formed from a plurality of glass fiber filaments, and wherein said random faults comprise broken filaments in said strand.

26. The detector apparatus of claim 24, wherein said amplifier mean in said detector circuit produces pulses having amplitudes proportional to the diameter of the broken filament being detected, said detector circuit further comprising a plurality of threshold circuits connected to the output of said amplifier means, each threshold circuit being set to respond to amplifier outputs of selected amplitudes to produce corresponding event pulses, and individual first counter means connected to each said threshold circuit to obtain counts of said broken filaments segmented by filament diameter.

27. The detector apparatus of claim 24, wherein said detector circuit further includes feedback means connected between said amplifier and said light source to maintain a predetermined amount of electrical output from the light receiver.

28. The detector apparatus of claim 27, further including intensity level detector means responsive to the level of current supplied to said light source, whereby degradation of said light beam due to the accumulation of foreign matter on said detector can be monitored.

29. The method of claim 25, wherein said strand is coated with a binder which is partially shed during the measurement of said broken filaments and accumulates as foreign matter on said detector.

30. The detector apparatus of claim 24, further including:
a plurality of optoelectronic detectors each having a light beam detecting source;
means for guiding a plurality of strands past said detectors and their associated light beam detecting sources, one strand for each said detector and associated light beam detecting source;
each said detector including a first counter for counting corresponding event pulses;

plural latch means, one latch means being connected to each said first counter; and means for periodically activating said latch means and for sequentially transferring the contents of said latch means to a processor.

31. Detector apparatus for determining with a high degree of reliability and accuracy the quality of an elongated article having random faults such as filament ends projecting therefrom, comprising:

an optoelectronic detector having a light source and a light receiver defining a light beam;

means for guiding an article to be measured along an article path past said detector and its light beam, said detector light beam being spaced from said article path sufficiently to prevent the article from interrupting said light beam, but being sufficiently close to said article path to enable random faults such as filament ends projecting from the article to interrupt said light beam;

circuit means connected to said light receiver to produce an event pulse for each interruption of said light beam, said circuit means including amplifier means connected to said light receiver, and level detector means having a predetermined threshold and being connected to the input of a storage means which level detector means produces an event pulse whenever its threshold is exceeded;

an integrator connected to the amplifier means to provide an integrator output which automatically regulates the light in said light source to maintain a predetermined amount of electrical output from the light receiver;

first counter means connected to said light detector means to count said event pulses;

latch means connected to said first counter means;

means periodically activating said latch means to temporarily store the content of said first counter means, for thereafter resetting said counter, and for transferring the content of said latch means to a processor; and second counter means for obtaining a unit of measure count for said random faults, and for transferring said unit of measure count to said processor for determining the number of events per unit of measure to thereby determine the quality of said article.

32. The detector apparatus of claim 31, wherein said processor includes storage means for accumulating said counts over a very large number of said units of measure so as to permit accumulation of a sufficient number of counts to enable a statistically significant average of events per unit of measure to be determined, whereby an accurate and reliable measure of quality can be obtained.

33. The detector apparatus of claim 31, wherein said second counter means measures units of time.

34. The detector apparatus of claim 31, wherein said second counter means measures the length of strand passing said detector, whereby said event unit of measure is a measure of broken filaments per unit length of said strand.

35. The detector apparatus of claim 31, wherein said means periodically activating said latch means is responsive to said second counter means to obtain event counts per unit of length from said first counter.

36. The detector apparatus of claim 35, wherein said storage means accumulates counts of events per unit length of said strand over a strand length on the order of one million yards to resolve quality differences of about 10 percent.

37. The detector apparatus of claim 35, wherein said storage means accumulates counts of events per unit length of said strand over a strand length on the order of 100 million yards to resolve quality differences of about one percent.

38. A method of determining with a high degree of reliability and accuracy the quality of an elongated article having random faults such as filament ends projecting outwardly therefrom, comprising:

moving an article to be measured at a high rate of speed along a path;

locating a detector including a detecting source having a beam adjacent said path, said detector and its beam being sufficiently far from said path as to prevent the article from activating said detecting source by interrupting said beam but sufficiently close to enable random faults to pass through said beam and activate said detecting source to produce corresponding event pulses;

accumulating a count for each of said event pulses recorded by an event pulse counter;

transferring the event pulse counts recorded to a first storage location at selected intervals and resetting said event pulse counter; and transferring each of the stored event pulse counts from the first storage to a second, processing storage location.

39. The method of claim 38, wherein the pulse counts stored in the processing storage location are processed therein to obtain an average number of event pulses per unit of time or of article length.

* * * * *